United States Patent [19]

Nakanishi et al.

[11] Patent Number: 5,589,491
[45] Date of Patent: Dec. 31, 1996

[54] INJECTION AND INJECTION KIT CONTAINING OMEPRAZOLE AND ITS ANALOGS

[75] Inventors: Shigeo Nakanishi, Neyagawa; Tetsuo Tominaga, Itami; Iwao Yamanaka, Osaka; Takashi Higo, Ikeda; Toshiyuki Shibata, Nakatsu, all of Japan

[73] Assignee: Astra Aktiebolag, Sodertalje, Sweden

[21] Appl. No.: 373,245

[22] PCT Filed: Jul. 15, 1993

[86] PCT No.: PCT/JP93/00998

§ 371 Date: Jan. 18, 1995

§ 102(e) Date: Jan. 18, 1995

[87] PCT Pub. No.: WO94/02141

PCT Pub. Date: Feb. 3, 1994

[30] Foreign Application Priority Data

Jul. 28, 1992 [JP] Japan .................................. 4-201203

[51] Int. Cl.$^6$ .......................... A61K 31/44; A61K 31/415
[52] U.S. Cl. ................................................... 514/338
[58] Field of Search .............................................. 514/338

[56] References Cited

U.S. PATENT DOCUMENTS

| 4,045,563 | 8/1977 | Berntsson et al. | 424/263 |
| 4,359,465 | 11/1982 | Ruwart | 424/263 |
| 4,472,409 | 9/1984 | Senn-Bilfinger | 424/263 |
| 4,628,098 | 12/1986 | Nohara et al. | 546/271 |
| 4,689,333 | 8/1987 | Nohara et al. | 514/338 |
| 4,738,974 | 4/1988 | Brändström | 514/338 |

FOREIGN PATENT DOCUMENTS

| 0005129 | 4/1981 | European Pat. Off. . |
| 0124495 | 11/1984 | European Pat. Off. . |
| 0356143 | 2/1990 | European Pat. Off. . |
| 0382489 | 8/1990 | European Pat. Off. . |
| 2134523 | 8/1984 | United Kingdom . |

Primary Examiner—Phyllis Spivack
Attorney, Agent, or Firm—White & Case

[57] ABSTRACT

An injection solution comprising a 2-[(2-pyridyl)methyl-sulfinyl]-benzimidazole compound or a salt thereof having antiulcer activity and an aqueous solvent added with no nonaqueous solvent is disclosed wherein the pH is not less than 9.5 and not more than 11.5.

6 Claims, No Drawings

INJECTION AND INJECTION KIT CONTAINING OMEPRAZOLE AND ITS ANALOGS

This application is a 371 of PCT/JP 93/00998 filed Jul. 15, 1993.

FIELD OF THE INVENTION

The present invention relates to an injection of a 2-[(2-pyridyl)methylsulfinyl]benzimidazole compound or a salt thereof having antiulcer activity, particularly sodium salt of omeprazole and to an injection kit thereof, which are used in clinical fields.

BACKGROUND OF THE INVENTION

The 2-[(2-pyridyl)methylsulfinyl]benzimidazole compounds such as omeprazole or lansoprazole are potent antiulcer agents, and are used as pharmaceutical compositions for oral administration. Further, the injections thereof have recently been developed.

As an injection of omeprazole, there has been known an injection prepared by dissolving sodium salt of omeprazole in sterilized water, filtering and lyophilizing the solution to give a lyophilized product, and then dissolving the lyophilized product in a mixture of polyethylene glycol 400 for injection, sodium dihydrogenphosphate and sterilized water (Japanese Patent Unexamined Publication No. 167587/1984).

Also, an injection prepared by dissolving a lyophilized product of an alkaline aqueous solution of a 2-[(2-pyridyl)methylsulfinyl]benzimidazole compound having antiulcer activity such as lansoprazole in a mixture of (a) acid, and (b) at least one of ethanol, propylene glycol and polyethylene glycol (Japanese Patent Unexamined Publication No. 138213/1990).

In general, the pH of injection is preferably about 4–8, and a pH above 9 has a probability of causing hemolysis and local irritation.

In the case of the 2-[(2-pyridyl)methylsulfinyl]benzimidazole compound or a salt which may be hereinafter referred to as "benzimidazole compound or salt thereof" represented by sodium salt of omepazole, it shows a solubility of the level permitting formulation of the preparation, in water in an alkaline range of pH 9.5 or above, whereas it shows extremely low solubility in water at a pH of not more than 9, thus rendering formulation of the preparation very difficult.

While the benzimidazole compound or salt thereof is stable in the alkaline range, it poses a problem in that its stability decreases with the low ph values.

For this reason, the method employed in conventional injections of benzimidazole compound or salt thereof such as sodium salt of omeprazole has been to add an acid such as hydrochloric acid or sodium dihydrogenphosphate to the solution to keep the pH from neutral to weak basic, and to further add a nonaqueous solvent such as polyethylene glycol, ethanol or propylene glycol in order to obtain a certain level of solubility in such pH range.

Yet, these injections pose problems of local irritation and hemolysis caused by the nonaqueous solvent added to the solution for dissolution.

Accordingly, an object of the invention is to provide an injection of a benzimidazole compound or a salt thereof, particularly sodium salt of omeprazole causing less side-effects such as hemolysis, and less local irritation, which salt permits easy formulation.

SUMMARY OF THE INVENTION

As a result of the intensive study conducted by the inventors with the aim of achieving the aforementioned object, it has now been found that a product obtained by lyophilizing an alkaline aqueous solution of benzimidazole compound or salt thereof, and dissolving same in an aqueous solvent being devoid of nonaqueous solvent scarcely shows hemolytic property and local irritation, notwithstanding the high pH of from 9.5 to 11.5.

Accordingly, the present invention is:

(1) an injection comprising a 2-[(2-pyridyl)methylsulfinyl]benzimidazole compound or a salt thereof having antiulcer activity and an aqueous solvent devoid of nonaqueous solvent, which has a pH of not less than 9.5 and not more than 11.5, (2) an injection kit comprising the following (a) and (b), wherein (a) and (b) are adjusted such that the pH upon dissolution of (a) in (b) is not less than 9.5 and not more than 11.5;

(a) : a lyophilized product of an alkaline aqueous solution of a 2-[(2-pyridyl)methylsulfinyl]benzimidazole compound or a salt thereof having antiulcer activity (b) : an aqueous solvent devoid of nonaqueous solvent.

DETAILED DESCRIPTION

The 2-[(2-pyridyl)methylsulfinyl]benzimidazole compounds having antiulcer activity which are the element constituting the present invention include, for example, the compounds described in Japanese Patent Unexamined Publication No. 62275/1977, Japanese Patent Unexamined Publication No. 1417/1979, Japanese Patent Unexamined Publication No. 53406/1982, Japanese Patent Unexamined Publication No. 135881/1983, Japanese Patent Unexamined Publication No. 192880/1983, Japanese Patent Unexamined Publication No. 181277/1984 or Japanese Patent Unexamined Publication No. 50978/1986, and omeprazole [chemical name: 2-[2-(3,5-dimethyl-4-methoxy)-pyridylmethylsulfinyl]-(5-methoxy)benzimidazole] and lansoprazole [chemical name: 2-{2-[(3-methyl-4-(2,2,2-trifluoroethoxy)]-pyridylmethylsulfinyl}-benzimidazole] are exemplified.

As the salts of said benzimidazole compounds, for example, salts of alkaline metal such as sodium salt or potassium salt or salts of alkaline earth metal such as calcium salt or magnesium salt.

In view of the solubility, it is preferable for the present invention to use the salt of benzimidazole compound.

The injection of the present invention has a pH of not less than 9.5 and not more than 11.5, preferably not less than 10 and not more than 11. Where the pH is less than 9.5, the benzimidazole compound or salt thereof does not sufficiently dissolve in an aqueous solvent and shows poor stability, while where it is more than 11.5, hemolytic property and local irritation become prominent.

According to the present invention, an injection of the benzimidazole compound or salt thereof can be prepared by dissolving the benzimidazole compound or salt thereof in water for injection, etc. along with a strong alkaline compound such as sodium hydroxide, potassium hydroxide, sodium carbonate or L-arginine, to give an alkaline aqueous solution having a pH adjusted to not less than 10.5 and not more than 12.5, preferably not less than 11 and not more than 12. The alkaline aqueous solution may contain mannitol, glycine, sorbitol, inositol, etc. on demand for better forming of a lyophilized product.

The benzimidazole compound is contained in said alkaline aqueous solution in a proportion of 1–50 mg/ml, preferably 5–40 mg/ml on a free compound basis.

Then, this alkaline aqueous solution is filtered for sterilization, and charged in a vial by 0.5–10 ml. After nitrogen gas displacement has been preformed as necessary, the solution is lyophilized by a method known per se. The lyophilized product thus obtained is the (a): a lyophilized product of an alkaline aqueous solution of the 2-[(2-pyridyl)methylsulfinyl]benzimidazole compounds or salt thereof having antiulcer activity to be contained in the injection kit of the present invention.

When in use, the injection of the present invention can be produced by dissolving the lyophilized product thus obtained in an aqueous solvent devoid of nonaqueous solvent, such as physiological saline, aqueous solution of 5% glucose, or distilled water for injection. Said aqueous solvent corresponds to the (b): an aqueous solvent added with no nonaqueous solvent to be contained in the injection kit of the present invention.

The injection of the present invention can be used, for example, in the form of drip infusion, intravenous injection, intramuscular injection, subcutaneous injection.

The concentration of benzimidazole compound in the injection of the present invention may vary depending upon the administration route, and generally ranges in a proportion of 0.05–10 mg/ml, preferably 0.1–5 mg/ml on a free compound basis.

The benzimidazole compound in the injection of the present invention is administered to an adult at 10–100 mg per day on a free compound basis in a single to three times divided doses, depending upon, for example, the symptoms of the patients.

BEST MODE FOR CARRYING OUT OF THE INVENTION

EXPERIMENTAL EXAMPLE 1

Test preparation
1. Preparation obtained in Example 1 to be mentioned later
Test method
1. Hemolysis test
   Hemolysis was evaluated by Akaishi method using whole blood of rabbit. The result is given in Table 1.
2. Local irritation test Local irritation was evaluated by the comparison of necrotic muscular tissue area at the injection site in 3 rabbits at 2 days after the administration of i ml of the test preparation by intramuscular injection, with that in the rabbits administered with i ml of physiological saline or 1 ml of a 1.7% acetic acid solution, respectively by intramuscular injection.

The results are summarized in Table 2.
Test results

TABLE 1

| Test preparation | pH | Hemolysis |
| --- | --- | --- |
| Ex. 1 | 10.5 | not observed |

TABLE 2

| Test preparation | pH | Necrotic area (mm$^2$) |
| --- | --- | --- |
| Ex. 1 | 10.5 | 63 |
| 1.7% acetic acid solution (positive comparison solution) | — | 398 |
| physiological | — | 31 |

TABLE 2-continued

| Test preparation | pH | Necrotic area (mm$^2$) |
| --- | --- | --- |
| saline (negative comparison solution) | | |

(average of 3 rabbits)

The preparation of the present invention is desirable as an injection, since it does not cause hemolysis at all despite the high pH, and causes less local irritation,

EXAMPLE 1

1N Sodium hydroxide (2.3 ml) is added to 21.3 g of sodium salt of omeprazole (20 g as omeprazole), and water for injection is added thereto to adjust the pH to 11.5 and the total amount to 1 kg.

After filtration for sterilization, this alkaline aqueous solution is charged in 10 ml vials by 2 g. A rubber plug is half driven in, and nitrogen displacement is performed. Lyophilization by a conventional method and dissolution of the lyophilized product obtained in 10 ml of physiological saline give an omeprazole injection [4 mg (free compound)/ml].

INDUSTRIAL APPLICABILITY

The injection of the present invention is void of the necessity to lower pH so as to prevent hemolysis and local irritation, and to add a nonaqueous solvent such as polyethylene glycol to an aqueous solvent for dissolution so as to prevent concomitant lowering of solubility. As a result, irritation and hemolysis caused by the nonaqueous solvent can be avoided. Accordingly, the injection of the present invention can secure solubility sufficient for formulation into preparation and safety for the human body.

We claim:

1. An injection solution comprising a 2-[(2-pyridyl)methylsulfinyl]benzimidazole compound or a salt thereof having antiulcer activity and an aqueous solvent devoid of nonaqueous solvent, wherein the pH of the injection solution is not less than 9.5 and not more than 11.5.

2. The injection solution of claim 1, wherein the 2-[(2-pyridyl)methylsulfinyl]benzimidazole compound or a salt thereof having antiulcer activity is in the form of a lyophilized product of the alkaline aqueous solution dissolved in the aqueous solvent devoid of nonaqueous solvent.

3. The injection solution of claim 1, wherein the 2-[(2-pyridyl)methylsulfinyl]benzimidazole salt is sodium salt of omeprazole.

4. The injection solution of claim 1, wherein the benzimidazole salt is selected from the group consisting of sodium, potassium, calcium, and magnesium.

5. An injection kit comprising the following components (a) and (b), in proportions such that the pH upon dissolution of (a) in (b) is not less than 9.5 and not more than 11.5; the components being (a) : a lyophilized product of an alkaline aqueous solution of a 2-[(2-pyridyl)methylsulfinyl]benzimidazole compound or a salt thereof having antiulcer activity (b) : an aqueous solvent devoid of nonaqueous solvent.

6. The injection kit of claim 5, wherein the 2-[(2-pyridyl)methylsulfinyl]benzimidazole salt is sodium salt of omeprazole.

* * * * *